United States Patent [19]
Johnson

[11] Patent Number: 5,192,792
[45] Date of Patent: Mar. 9, 1993

[54] ISATINE DERIVATIVES, AND THEIR METHOD OF USE

[75] Inventor: Graham Johnson, Ann Arbor, Mich.

[73] Assignee: Warner-Lambert Company, Morris Plains, N.J.

[21] Appl. No.: 624,157

[22] Filed: Dec. 7, 1990

[51] Int. Cl.$^5$ .................... A61K 31/40; C07D 209/04; C07D 209/56

[52] U.S. Cl. .................... 514/418; 548/483; 548/450; 514/411

[58] Field of Search ................ 548/483, 450; 514/418, 514/411

[56] References Cited

FOREIGN PATENT DOCUMENTS

WO8903818  5/1989  PCT Int'l Appl. ................ 548/483

OTHER PUBLICATIONS

CA 78:124421k Antiviral Substances, Carbamoyloximine derivatives of isatin and its heterocyclic analogs, Giannella et al. 1973.
Wiss Z, Ernst-Moritz-Arndt, University of Greifswald, Math.-nat.wiss. Reihe 35, 39-44, (1986) 4.
Pharmazie 39, H. 10, 713 (1984), Fisher et al.
Pharmazie 37, H. 12, 858-861 (1982), Fischer et al.
Neuroscience Letters 107, 327-330 (1989), Clow et al.
Khim.-Farm.zh. 23(11), 1349-2352 (1989).

Primary Examiner—Mary C. Lee
Assistant Examiner—Joseph K. McKane
Attorney, Agent, or Firm—Ronald A. Daignault

[57] ABSTRACT

A method of treatment of central nervous system disorders with compounds having the formula

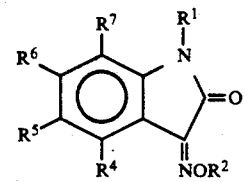

and isomers thereof wherein $R^1$, $R^2$, $R^4$, $R^5$, $R^6$, and $R^7$ and as defined in the specification; as well as pharmaceutical compositions thereof.

16 Claims, No Drawings

ISATINE DERIVATIVES, AND THEIR METHOD OF USE

The present invention relates to a method of treatment with compounds having excitatory amino acid antagonizing properties, pharmaceutical compositions comprising such compounds, and to novel compounds having excitatory amino acid antagonizing properties and to the preparation of such compounds.

It is an object of the present invention to provide a method of treating diseases in mammals, including a human, by antagonizing an excitatory amino acid in such mammal.

A second object of the present invention is to provide novel pharmaceutical compositions useful for the treatment of diseases in mammals, including a human, acting by antagonizing an excitatory amino acid in such mammal.

A third object of the present invention is to provide novel compounds useful for the treatment of diseases in mammals, including a human, acting by antagonizing an excitatory amino acid in such mammal.

BACKGROUND OF THE INVENTION

It is well known from Wiss Z, Ernst-Moritz-Arndt - University of Greifswald, Math.-nat.wiss. Reihe 35, 39–44 (1986) 4, Pharmazie 39, H.10, 713 (1984), Pharmazie 37, H.12, B58-861 (1982), Neuroscience Letters 107, 327–330 (1989), PCT patent application International Publication Number WO 89/03818, and Khim.-Farm.zh. 23(11), 1349-1352 (1989), that certain of the chemical entities comprised within the scope of method of treatment according to the present invention are known to possess biological activity.

SUMMARY OF THE INVENTION

The invention then, inter alia, comprises the following, alone or in combination:

A method of antagonizing the biological effects of an excitatory amino acid of a subject in need of such antagonization comprising the step of administering the said subject an effective excitatory amino acid antagonizing amount of an indole-2,3-dione-3-oxime compound having the formula

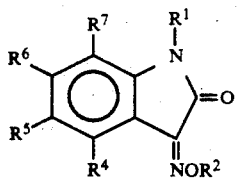

wherein
$R^1$ is hydrogen, $C_{1-6}$-alkyl which may be branched, $C_{3-7}$-cyclo-alkyl, benzyl, phenyl which may be substituted, acyl, hydroxy, $C_{1-6}$-alkoxy, $CH_2CO_2R'$ wherein $R'$ is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, or $CH_2C(=NOH)NH_2$;

$R^2$ is (1) alkenyl of from two to six carbon atoms, preferably allyl, (2) alkynyl of from two to six carbons, preferably propargyl, (3) $(CH_2)_{1-6} CO_2H$, (4) $(CH_2)_{1-6}CONHR$ wherein R is $C_{1-6}$alkyl, optionally branched; aryl which is phenyl optionally substituted by one or more of lower alkyl of from one to four carbons, halogen wherein halogen is fluoro, chloro, bromo, or iodo, trifluoromethyl, cyano, carboxy, alkoxycarbonyl wherein the alkoxy is of from one to four carbons, alkylthio wherein the alkyl is of from one to four carbons, nitro, acyl of from two to four carbons, hydroxy, $C_{1-6}$-alkoxy, $CH_2CO_2R'$ wherein $R'$ is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, optionally branched; aralkyl which is aryl as defined above attached through $C_{1-4}$alkyl; or $SO_2R^{10}$ wherein $R^{10}$ is $C_{1-6}$alkyl, optionally branched; aryl which is phenyl optionally substituted by one or more of lower alkyl of from one to four carbons, halogen wherein halogen is fluoro, chloro, bromo, or iodo, trifluoromethyl, cyano, carboxy, alkoxycarbonyl wherein the alkoxy is of from one to four carbons, alkylthio wherein the alkyl is of from one to four carbons nitro, acyl of from two to four carbons, hydroxy, $C_{1-6}$-alkoxy, $CH_2CO_2R'$ wherein $R'$ is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, optionally branched; aralkyl which is aryl as defined above attached through $C_{1-4}$alkyl;

$R_4, R_5, R_6, R_7$ independently are hydrogen, $C_{1-6}$-aklyl, which may be branched, phenyl, halogen, $C_{1-6}$-alkoxy, $NO_2$, CN, $CF_3$, or $SO_2NR''R'''$ wherein $R''$ and $R'''$ independently are hydrogen or $C_{1-6}$-alkyl; or $R^6$ and $R^7$ together form an additional 4- to 7 -membered ring which may be aromatic or partial saturated and which may be substituted with halogen, $NO_2$, $CF_3$, CN, $SR_2NR''R'''$ wherein $R''$ and $R'''$ independently are hydrogen or $C_{1-6}$-alkyl, and $R^4$ and $R^5$ have the meanings set forth above, a method as above wherein at least one of $R^4$, $R^5$, $R^6$, or $R^7$ is an electron withdrawing substituent such as $NO_2^2$, $CF_3$, CN, $SO_2NR''R'''$, or halogen and $R^1$, $R^2$, $R^4$, $R^5$, $R^6$, $R^7$, $R''$, and $R'''$ otherwise have the meanings set forth, a method as first above wherein $R^5$ is $NO_2$, F, $CF_3$, or CN, moreover a method of antagonizing the biological effects of an excitatory amino acid as first above, wherein the compound is administered in the form of a pharmaceutical composition thereof, in which it is present together with a pharmaceutically acceptable carrier or diluent, and a method of antagonizing the biological effects of an excitatory amino acid as second above, wherein the compound is administered in the form of a pharmaceutical composition thereof, in which it is present together with a pharmaceutically acceptable carrier or diluent, and a method of antagonizing the biological effects of an excitatory amino acid as second above, wherein the compound is administered in the form of a pharmaceutical composition thereof, in which it is present together with a pharmaceutically acceptable carrier or diluent, further a pharmaceutical composition for use in antagonizing the biological effects of an excitatory amino acid of a subject in need of such antagonization comprising an effective excitatory amino acid antagonizing amount of a compound having the formula

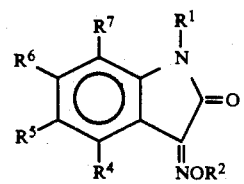

$R^1$ is hydrogen;

$R^2$ is (1) alkenyl of from two to six carbon atoms, preferably allyl, (2) alkynyl of from two to six carbons, preferably propargyl, (3) $(CH_2)_{1-6}CO_2H$, (4) $(CH_2)_{1-6}CONHR$ wherein R is $C_{1-6}$alkyl, optionally branched; aryl which is phenyl optionally substituted by one or more of lower alkyl of from one to four carbons, halogen wherein halogen is fluoro, chloro, bromo, or iodo, trifluoromethyl, cyano, carboxy, alkoxycarbonyl wherein the alkoxy is of from one to four carbons, alkylthio wherein the alkyl is of from one to four carbons, nitro, acyl of from two to four carbons, hydroxy, $C_{1-6}$-alkoxy, $CH_2CO_2R'$ wherein $R'$ is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, optionally branched; aralkyl which is aryl as defined above attached through $C_{1-4}$alkyl; or $SO_2R^{10}$ wherein $R^{10}$ is $C_{1-6}$alkyl, optionally branched; aryl which is phenyl optionally substituted by one or more of lower alkyl of from one to four carbons, halogen wherein halogen is fluoro, chloro, bromo, or iodo, trifluoromethyl, cyano, carboxy, alkoxycarbonyl wherein the alkoxy is of from one to four carbons, alkylthio wherein the alkyl is of from one to four carbons, nitro, acyl of from two to four carbons, hydroxy, $C_{1-6}$-alkoxy, $CH_2CO_2R'$ wherein $R'$ is hydrogen or $C_{1-6}$-alkyl which may be branched, $CH_2CN$, $CH_2$, $CONR^{IV}R^V$ wherein $R^{IV}$ and $R^V$ independently are hydrogen or $C_{1-6}$-alkyl, optionally branched; aralkyl which is aryl as defined above attached through $C_{1-4}$alkyl;

$R^4$, $R^5$, $R^6$, $R^7$ independently are hydrogen, $C_{1-6}$-alkyl which may be branched, phenyl, halogen, $C_{1-6}$-alkoxy, $NO_2$, $CN$, $SO_2NR''R'''$ wherein $R''$ and $R'''$ independently are hydrogen or $C_{1-6}$-alkyl, or $CF_3$, or $R^6$ and $R^7$ together form an additional 4- to 7-membered ring which may be aromatic or partial saturated and which may be substituted with halogen, $NO_2$, $CF_3$, $CN$, $SO_2NR''R'''$ wherein $R''$ and $R'''$ independently are hydrogen or $C_{1-6}$-alkyl, and $R^4$ and $R^5$ have the meanings set forth above, at least one of $R^4$, $R^6$, and $R^7$ are other than hydrogen when $R^5$ is not other than H, Cl, or Br; or $R^1$ is $C_{1-6}$-alkyl which may be branched, $C_{3-7}$-cycloalkyl, benzyl, phenyl which may be substituted, acyl, hydroxy, $C_{1-6}$-alkoxy, $CH_2CO_2R'$ wherein R; is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, $CH_2C(=NOH)NH_2$;

$R^2$ is (1) alkenyl of from two to six carbon atoms, preferably allyl, (2) alkynyl of from two to six carbons, preferably propargyl, (3) $(CH_2)_{1-6}CO_2H$, (4) $(CH_2)_{1-6}CONHR$ wherein R is $C_{1-6}$alkyl, optionally branched; aryl which is phenyl optionally substituted by one or more of lower alkyl of from one to four carbons, halogen wherein halogen is fluoro, chloro, bromo, or iodo, trifluoromethyl, cyano, carboxy, alkoxycarbonyl wherein the alkoxy is of from one to four carbons, alkylthio wherein the alkyl is of from one to four carbons, nitro, acyl of from two to four carbons, hydroxy, $C_{1-6}$-alkoxy, $CH_2CO_2R'$ wherein $R'$ is hydrogen or $C_{1-6}$-alkyl which may be branched, $CH_2CN$, $CH_2$, $CONR^{IV}R^V$ wherein $R^{IV}$ and $R^V$ independently are hydrogen or $C_{1-6}$-alkyl, optionally branched; aralkyl which is aryl as defined above attached through $C_{1-4}$alkyl; or $SO_2R^{10}$ wherein $R^{10}$ is $C_{1-6}$alkyl, optionally branched; aryl which is phenyl optionally substituted by one or more of lower alkyl of from one to four carbons, halogen wherein halogen is fluoro, chloro, bromo, or iodo, trifluoromethyl, cyano, carboxy, alkoxycarbonyl wherein the alkoxy is of from one to four carbons, alkylthio wherein the alkyl is of from one to four carbons, nitro, acyl of from two to four carbons, hydroxy, $C_{1-6}$-alkoxy, $CH_2CO_2R'$ wherein $R'$ is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, optionally branched; aralkyl which is aryl as defined above attached through $C_{1-4}$alkyl;

$R^4$, $R^5$, $R^6$, $R^7$ independently are hydrogen $C_{1-6}$-alkyl which may be branched, phenyl, halogen, $C_{1-6}$-alkoxy, $NO_2$, $CN$, $SO_2NR''R'''$ wherein $R''$ and $R'''$ independently are hydrogen or $C_{1-6}$-alkyl, or $CF_3$, or $R^6$ and $R^7$ together form an additional 4- to 7-membered ring which may be aromatic or partial saturated and which may be substituted with halogen, $NO_2$, $CF_3$, $CN$, $SO_2NR'R'''$ wherein $R''$ and $R'''$ independently are hydrogen or $C_{1-6}$-alkyl, and $R^4$ and $R^5$ have the meanings set forth above, at least one of $R^4$, $R^5$, $R^6$, and $R^7$ are other than hydrogen when $R^1$ is not other than methyl, at least one of $R^4$ and $R^5$ are Other than hydrogen when $R^1$ is not other than phenyl which may be substituted, and at least one of $R^4$ and $R^5$ are other than hydrogen when $R^6$ and $R^7$ together form an additional benzene ring, and method of antagonizing the biological effects of an excitatory amino acid of a subject in need thereof comprising the step of administering the said subject a pharmaceutical composition as above, further a compound having the formula

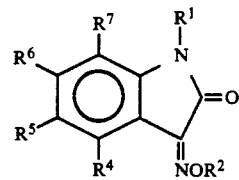

wherein $R^1$ is $C_{1-6}$-alkyl which may be branched, $C_{3-7}$-cycloalkyl, benzyl, phenyl which may be substituted, acyl, hydroxy, $C_{1-6}$-alkoxy, $CH_2CO_2R'$ wherein $R'$ is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, or $CH_2C(=NOH)NH_2$;

$R^2$ is (1) alkenyl of from two to six carbon atoms, preferably allyl, (2) alkynyl of from two to six carbons, preferably propargyl, (3) $(CH_2)_{1-6}CO_2H$, (4) $(CH_2)_{1-6}CONHR$ wherein R is $C_{1-6}$alkyl, optionally branched; aryl which is phenyl optionally substituted by one or more of lower alkyl of from one to four carbons, halogen wherein halogen is fluoro, chloro, bromo, or iodo, trifluoromethyl, cyano, carboxy, alkoxycarbonyl wherein the alkoxy is of from one to four carbons, alkylthio wherein the alkyl is of from one to four carbons, nitro, acyl of from two to four carbons, hydroxy, $C_{1-6}$-alkoxy, $CH_2CO_2R'$ wherein $R'$ is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, optionally branched; aralkyl which is aryl as defined above attached through $C_{1-4}$alkyl; or $SO_2R^{10}$ wherein $R^{10}$ is $C_{1-6}$alkyl, optionally branched; aryl which is phenyl optionally substituted by one or more of lower alkyl of from one to four carbons, halogen wherein halogen is fluoro, chloro, bromo, or iodo, trifluoromethyl, cyano, carboxy, alkoxycarbonyl wherein the alkoxy is of from one to four carbons, alkylthio wherein the alkyl is of from one to four carbons, nitro, acyl of from two to four carbons, hydroxy, $C_{1-6}$-alkoxy, $CH_2CO_2R'$ wherein R' is hydrogen or $C_{1-6}$-alkyl which may be branched, $CH_2CN$, $CH_2$, $CONR^{IV}R^V$ wherein $R^{IV}$ and $R^V$ independently are hydrogen or $C_{1-6}$-alkyl, optionally branched; aralkyl which is aryl as defined above attached through $C_{1-4}$alkyl;

$R_5$ is $NO_2$, F, $CF_3$, $SO_2NR''R'''$ wherein R'' and R''' independently are hydrogen or $C_{1-6}$-alkyl, or CN; and $R^4$, $R^6$, $R^7$ independently are hydrogen, $C_{1-6}$-alkyl which may be branched, phenyl, halogen, $C_{1-6}$-alkoxy, $NO_2$, CN, $SO_2NR''R'''$ wherein R'' and R''' independently are hydrogen or $C_{1-6}$-alkyl, or $CF_3$, or $R^6$ and together form an additional 4 to 7-membered ring which may be aromatic or partial saturated and which may be substituted with halogen, $NO_2$, $CF_3$, CN, $SO_2NR''R'''$ wherein R'' and R''' independently are hydrogen or $C_{1-6}$-alkyl, $R_4$ has the meaning set forth above, and a compound having the formula

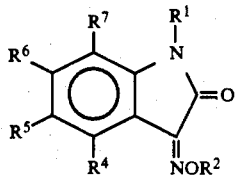

wherein $R^1$ is $C_{1-6}$-alkyl which may be branched, $C_{3-7}$-cycloalxyl, benzyl, acyl, hydroxy, $C_{1-6}$-alkoxy, $CH_2CO_2R'$ wherein R' is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, or $CH_2CH(=NOH)NH_2$;

$R^2$ is (1) alkenyl of from two to six carbon atoms, preferably allyl, (2) alkynyl of from two to six carbons, preferably propargyl, (3) $(CH_2)_{1-6}$ $CO_2H$, (4) $(CH_2)_{1-6}CONHR$ wherein R is $C_{1-6}$alkyl, optionally branched; aryl which is phenyl optionally substituted by one or more of lower alkyl of from one to four carbons, halogen wherein halogen is fluoro, chloro, bromo, or iodo, trifluoromethyl, cyano, carboxy, alkoxycarbonyl wherein the alkoxy is of from one to four carbons, alkylthio wherein the alkyl is of from one to four carbons, nitro, acyl of from two to four carbons, hydroxy, $C_{1-6}$-alkoxy, $CH_2CO_2R'$ wherein R' is hydrogen or $C_{1-6}$-alkyl which may be branched, $CH_2CN$, $CH_2,CONR^{IV}R^V$ wherein $R^{IV}$ and $R^V$ independently are hydrogen or $C_{1-6}$-alkyl, optionally branched; aralkyl which is aryl as defined above attached through $C_{1-4}$alkyl; or $SO_2R^{10}$ wherein $R^{10}$ is $C_{1-6}$alkyl, optionally branched; aryl which is phenyl optionally substituted by one or more of lower alkyl of from one to four carbons, halogen wherein halogen is fluoro, chloro, bromo, or iodo, trifluoromethyl, cyano, carboxy, alkoxycarbonyl wherein the alkoxy is of from one to four carbons, alkylthio wherein the alkyl is of from one to four carbons, nitro, acyl of from two to four carbons, hydroxy, $C_{1-6}$-alkoxy, $CH_2CO_2R'$ wherein R' is hydrogen or $C_{1-6}$-alkyl which may be branched, $CH_2CN$, $CH_2,CONR^{IV}R^V$ wherein $R^{IV}$ and $R^V$ independently are hydrogen or $C_{1-6}$-alkyl, optionally branched; aralkyl which is aryl as defined above attached through $C_{1-4}$alkyl;

$R^5$ is $NO_2$, F, $CF_3$, $SO_2NR'R'''$ wherein R'' and R''' independently are hydrogen or $C_{1-6}$-alkyl, or CN; and $R^4$, $R^6$, $R^7$ independently are hydrogen, $C_{1-6}$-alkyl which may be branched, phenyl, halogen, $C_{1-6}$-alkoxy, $NO_2$, CN, $SO_2NR''R'''$ wherein R'' and R''' independently are hydrogen or $C_{1-6}$-alkyl, or $CF_3$, or $R^6$ and together form an additional 4 to 7 membered ring which may be aromatic or partial saturated and which may be substituted with halogen, $NO_2$, $CF_3$, CN, $SO_2NR''R'''$ wherein R'' and R''' independently are hydrogen or $C_{1-6}$-alkyl, and $R^4$ has the meaning set forth above, and a compound having the formula

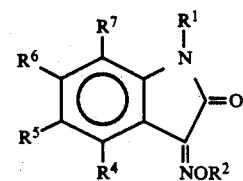

wherein $R^1$ is hydrogen, $R^2$ is (1) alkenyl of from two to six carbon atoms, preferably allyl, (2) alkynyl of from two to six carbons, preferably propargyl, (3) $(CH_2)_{1-6}$ $CO_2H$, (4) $(CH_2)_{1-6}CONHR$ is $C_{1-6}$alkyl, optionally (4) $(CH_2)_{1-6}CONHR$ wherein branched; aryl which is phenyl optionally substituted by one or more of lower alkyl of from one to four carbons, halogen wherein halogen is fluoro, chloro, bromo, or iodo, trifluoromethyl, cyano, carboxy, alkoxycarbonyl wherein the alkoxy is of from one to four carbons, alkylthio wherein the alkyl is of from one to four carbons, nitro, acyl of from two to four carbons, hydroxy, $C_{1-6}$-alkoxy, $CH_2CO_2R'$ wherein R' is hydrogen or $C_{1-6}$-alkyl which may be branched, $CH_2CN$, $CH_2,CONR^{IV}R^V$ wherein $R^{IV}$ and $R^V$ independently are hydrogen or $C_{1-6}$-alkyl, optionally branched; aralkyl which is aryl as defined above attached through $C_{1-4}$alkyl; or $SO_2R^{10}$ wherein $R^{10}$ is $C_{1-6}$alkyl, optionally branched; aryl which is phenyl optionally substituted by one or more of lower alkyl of from one to four carbons, halogen wherein halogen is fluoro, chloro, bromo, or iodo, trifluoromethyl, cyano, carboxy, alkoxycarbonyl wherein the alkoxy is of from one to four carbons, alkylthio wherein the alkyl is of from one to four carbons, nitro, acyl of from two to four carbons hydroxy, $C_{1-6}$-alkoxy, $CH_2CO_2R'$ wherein R' is hydrogen or $C_{1-6}$-alkyl which may be branched, $CH_2CN$, $CH_2$, $CONR^{IV}R^V$ wherein $R^{IV}$ and $R^V$ independently are hydrogen or $C_{1-6}$-alkyl, optionally branched; aralkyl which is aryl as defined above attached through $C_{1-4}$alkyl;

$R^5$ is $NO_2$, F, $CF_3$, $SO_2NR''R'''$ wherein R'' and R''' independently are hydrogen or $C_{1-6}$-alkyl, or CN; and $R^4$, $R^6$, $R^7$ independently are hydrogen $C_{1-6}$-alkyl which may be branched, phenyl, halogen, $C_{1-6}$-alkoxy, $NO_2$, CN, $SO_2NR''R'''$ wherein R'' and R''' independently are hydrogen or $C_{1-6}$-alkyl, or $CF_3$, or $R^6$ and together form an additional 4 to 7 membered ring which may be aromatic or partial saturated and which may be substituted with halogen, $NO_2$, $CF_3$, CN, $SO_2NR''R'''$ wherein R'' and R''' independently are hydrogen or $C_{1-6}$-alkyl, and $R^4$ has the meaning set forth above, and that $R^5$ is different from NO₂ and F when R¹, R⁴, R⁶, and are not other than hydrogen and R² is (1) alkenyl of from two to six carbon atoms, preferably allyl, (2) alkynyl of from two to six carbons, preferably propargyl, (3) $(CH_2)_{1-6}CO_2H$, (4) $(CH_2)_{1-6}CONHR$ wherein R is $C_{1-6}$alkyl, optionally branched; aryl which is phenyl optionally substituted by one or more of lower alkyl of from one to four carbons, halogen wherein halogen is fluoro, chloro, bromo, or iodo, trifluoromethyl, cyano, carboxy, alkoxycarbonyl wherein the alkoxy is of from one to four carbons, alkylthio wherein the alkyl is of from one to four carbons, nitro, acyl of from two to four carbons, hydroxy, $C_{1-6}$-alkoxy, $CH_2CO_2R'$ wherein R' is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, optionally branched; aralkyl which is aryl as defined above attached through $C_{1-4}$alkyl; or $SO_2R^{10}$ wherein $R^{10}$ is $C_{1-6}$alkyl, optionally branched; aryl which is phenyl optionally substituted by one or more of lower alkyl of from one to four carbons, halogen wherein halogen is fluoro, chloro, bromo, or iodo, trifluoromethyl, cyano, carboxy, alkoxycarbonyl wherein the alkoxy is of from one to four carbons, alkylthio wherein the alkyl is of from one to four carbons, nitro, acyl of from two to four carbons, hydroxy, $C_{1-6}$-alkoxy, $CH_2CO_2R'$ wherein R' is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, optionally branched; aralkyl which is aryl as defined above attached through $C_{1-4}$alkyl; and R⁵ is different from NO₂ when R¹, R², R⁴, and R⁶ are not other than hydrogen and is not other than NO₂, further a compound as above wherein R⁴ and R⁵ independently are hydrogen, F, NO₂, CN, CF₃, or $SO_2NR''R'''$ wherein R'' and R''' independently are hydrogen or $C_{1-6}$-alkyl, and wherein R⁶ and together form an additional 4 to 7 membered ring which may be aromatic or partial saturated and which may be substituted with halogen, NO₂, CF₃, CN, $SO_2NR''R'''$ wherein R'' and R''' independently are hydrogen or $C_{1-6}$-alkyl, and a compound as above wherein the additional ring formed by R⁶ and is substituted with halogen, NO₂, CF₂, CN, or $SO_2NR''R'''$ wherein R'' and R''' independently are hydrogen or $C_{1-6}$-alkyl, and a compound as above, which is 5-nitro-1H-benz[g]indole-2,3-dione-3-oxime, and a compound as above, which is 5,7-dinitro-1-methyl-1H-indole-2,3-dione-3-(O-methyloxime), and a compound as above, which is 5-nitro-1H-6,7,8,9-tetra-hydro-benz[g]indole-2,3-dione-3-oxime, moreover a method of treating a central nervous system disorder in a subject in need of such treatment, comprising the step of administering to said subject an effective amount of a compound having the formula

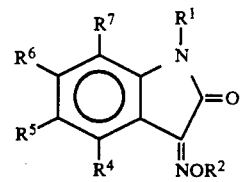

wherein
R¹ is hydrogen, $C_{1-6}$-alkyl which may be branched, $C_{3-7}$-cycloalkyl, benzyl, phenyl which may be substituted, acyl, hydroxy, $C_{1-6}$-alkoxy, $CH_2CO_2R'$ wherein R' is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$alkyl, or $CH_2C(=NOH)NH_2$;

R² is (1) alkenyl of from two to six carbon atoms, preferably allyl, (2alkynyl of from two to six carbons, preferably propargyl, (3) $(CH_2)_{1-6}CO_2H$, (4) $(CH_2)_{1-6}CONHR$ wherein R is $C_{1-6}$alkyl, optionally branched; aryl which is phenyl optionally substituted by one or more of lower alkyl of from one to four carbons, halogen wherein halogen is fluoro, chloro, bromo, or iodo, trifluoromethyl, cyano, carboxy, alkoxycarbonyl wherein the alkoxy is of from one to four carbons, alkylthio wherein the alkyl is of from one to four carbons, nitro, acyl of from two to four carbons, hydroxy, $C_{1-6}$-alkoxy, $CH_2CO_2R'$ wherein R' is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, optionally branched; aralkyl which is aryl as defined above attached through $C_{1-4}$alkyl; or $SO_2R^{10}$ wherein $R^{10}$ is $C_{1-6}$alkyl, optionally branched; aryl which is phenyl optionally substituted by one or more of lower alkyl of from one to four carbons, halogen wherein halogen is fluoro, chloro, bromo, or iodo, trifluoromethyl, cyano, carboxy, alkoxycarbonyl wherein the alkoxy is of from one to four carbons, alkylthio wherein the alkyl is of from one to four carbons, nitro, acyl of from two to four carbons, hydroxy, $C_{1-6}$-alkoxy, $CH_2CO_2R'$ wherein R' is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, optionally branched; aralkyl which is aryl as defined above attached through $C_{1-4}$alkyl;

R⁵ is NO₂, F, CF₃, $SO_2N''R'''$ wherein R'' and R''' independently are hydrogen or $C_{1-6}$-alkyl, or CN; and R⁴, R⁶, R⁷ independently are hydrogen $C_{1-6}$alkyl which may be branched, phenyl, halogen, $C_{1-6}$-alkoxy, NO₂, CN, $SO_2NR''R'''$ wherein R'' and R''' independently are hydrogen or $C_{1-6}$-alkyl, or CF₃, or R⁶ and together form an additional 4 to 7 membered ring which may be aromatic or partial saturated and which may be substituted with halogen, NO₂, CF₃, CN, $SO_2NR''R'''$ wherein R'' and R'' independently are hydrogen or $C_{1-6}$-alkyl, and R⁴ has the meaning set forth above; and that R⁵ is different from NO₂ and F when R¹, R⁴, R⁶, and are not other than hydrogen and R² is not other than hydrogen or benzyl; and that R⁵ is different from NO₂ when R¹, R², R⁴, and R⁶ are not other than hydrogen and is not other than NO₂, further a method of preparing a compound having the formula

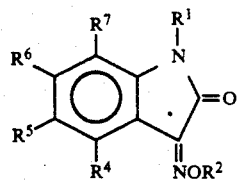

wherein
R$^1$ is hydrogen, C$_{1-6}$-alkyl which may be branched, C$_{3-7}$-cycloalkyl, benzyl, phenyl which may be substituted, acyl, hydroxy, C$_{1-6}$-alkoxy, CH$_2$CO$_2$R' wherein R' is hydrogen or C$_{1-6}$-alkyl which may be branched, CH$_2$CN, CH$_2$CONR$^{IV}$R$^V$ wherein R$^{IV}$ and R$^V$ independently are hydrogen or C$_{1-6}$-alkyl, or CH$_2$C(=NOH)NH$_2$;

R$^2$ is (1) alkenyl of from two to six carbon atoms, preferably allyl, (2) alkynyl of from two to six carbons, preferably propargyl, (3) (CH2)1-6 CO2H, (4) (CH2)1-6CONHR wherein R is C$_{1-6}$alkyl, optionally branched; aryl which is phenyl optionally substituted by one or more of lower alkyl of from one to four carbons, halogen wherein halogen is fluoro, chloro, bromo, or iodo, trifluoromethyl, cyano, carboxy, alkoxycarbonyl wherein the alkoxy is of from one to four carbons, alkylthio wherein the alkyl is of from one to four carbons, nitro, acyl of from two to four carbons, hydroxy, C$_{1-6}$-alkoxy, CH$_2$CO$_2$R' wherein R' is hydrogen or C$_{1-6}$-alkyl which may be branched, CH$_2$CN, CH$_2$CONR$^{IV}$R$^V$ wherein R$^{IV}$ and R$^V$ independently are hydrogen or C$_{1-6}$-alkyl, optionally branched; aralkyl which is aryl as defined above attached through C$_{1-4}$alkyl; or SO$_2$R$^{10}$ wherein R$^{10}$ is C$_{1-6}$alkyl, optionally branched; aryl which is phenyl optionally substituted by one or more of lower alkyl of from one to four carbons, halogen wherein halogen is fluoro, chloro, bromo, or iodo, trifluoromethyl, cyano, carboxy, alkoxycarbonyl wherein the alkoxy is of from one to four carbons, alkylthio wherein the alkyl is of from one to four carbons, nitro, acyl of from two to four carbons, hydroxy, C$_{1-6}$-alkoxy, CH$_2$CO$_2$R' wherein R' is hydrogen or C$_{1-6}$-alkyl which may be branched, CH$_2$CN, CH$_2$CONR$^{IV}$R$^V$ wherein R$^{IV}$ and R$^V$ independently are hydrogen or C$_{1-6}$-alkyl, optionally branched; aralkyl which is aryl as defined above attached through C$_{1-4}$alkyl;

R$^5$ is NO$_2$, F, CF$_3$, SO$_2$NR"R"' wherein R" and R"' independently are hydrogen or C$_{1-6}$-alkyl, or CN; and R$^4$, R$^6$, R$^7$ independently are hydrogen, C$_{1-6}$-alkyl, which may be branched, phenyl, halogen, C$_{1-6}$-alkoxy, NO$_2$, SO$_2$NR"R"' wherein R" and R"' independently are hydrogen or C$_{1-6}$-alkyl, or CF$_3$, or R$^6$ and together form an additional 4 to 7 membered ring which may be aromatic or partial saturated and which may be substituted with halogen, NO$_2$, CF$_3$, CN, SO$_2$NR"R"' wherein R" and R"' independently are hydrogen or C$_{1-6}$-alkyl, and R$^4$ has the meaning set forth above; and that R$^5$ is different from NO$_2$ and F when R$^1$, R$^4$, R$^6$, and are not other than hydrogen and R$^2$ is (1) alkenyl of from two to six carbon atoms, preferably allyl, (2) alkynyl of from two to six carbons, preferably propargyl, (3) (CH2)1-6 CO2H, (4) (CH2)1-6CONHR wherein R is C$_{1-6}$alkyl, optionally branched; aryl which is phenyl optionally substituted by one or more of lower alkyl of from one to four carbons, halogen wherein halogen is fluoro, chloro, bromo, or iodo, trifluoromethyl, cyano, carboxy, alkoxycarbonyl wherein the alkoxy is of from one to four carbons, alkylthio wherein the alkyl is of from one to four carbons, nitro, acyl of from two to four carbons, hydroxy, C$_{1-6}$-alkoxy, CH$_2$CO$_2$R' wherein R' is hydrogen or C$_{1-6}$-alkyl which may be branched, CH$_2$CN, CH$_2$CONR$^{IV}$R$^V$ wherein R$^{IV}$ and R$^V$ independently are hydrogen or C$_{1-6}$ alkyl, optionally branched; aralkyl which is aryl as defined above attached through C$_{1-4}$alkyl;; or SO$_2$R$^{10}$ wherein R$^{10}$ is C$_{1-6}$alkyl, optionally branched; aryl which is phenyl optionally substituted by one or more of lower alkyl, halogen, wherein halogen is thiono, chloro, bromo, or iodo, trifluoromethyl, cyano, carboxy, alkoxycarbonyl, wherein the alkoxy is of from one to four carbons, alkylthio, wherein the alkyl is of from one to four carbons, nitro, acyl of from two to four carbons, hydroxy, C$_{1-6}$alkoxy, CH$_2$CO$_2$R' wherein R' is hydrogen or C$_{1-6}$-alkyl which may be branched, CH$_2$CN, CH$_2$CONR$^{IV}$R$^V$ wherein R$^{IV}$ and R$^V$ independently are hydrogen or C$_{1-6}$-alkyl, optionally branched; aralkyl which is aryl as defined above attached through C$_{1-4}$alkyl; and that R$^5$ is different from NO$_2$ when R$^1$, R$^2$, R$^4$, and R$^6$ are not other than hydrogen and is not other than NO$_2$, further a method of preparing a compound having the formula

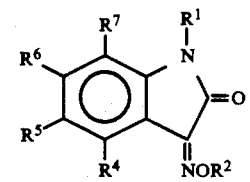

wherein
R$^1$ is hydrogen, C$_{1-6}$-alkyl which may be branched, C$_{3-7}$-cycloalkyl, benzyl, phenyl which may be substituted, acyl, hydroxy, C$_{1-6}$ alkoxy, CH$_2$CO$_2$R' wherein R' is hydrogen or C$_{1-6}$-alkyl which may be branched, CH$_2$CN, CH$_2$CONR$^{IV}$R$^V$ wherein R$^{IV}$ and R$^V$ independently are hydrogen or C$_{1-6}$-alkyl, or CH$_2$C(=NOH)NH$_2$;

R$^2$ is (1) alkenyl of from two to six carbon atoms, preferably allyl, (2) alkynyl of from two to six carbons, preferably propargyl, (3) (CH$_2$)$_{1-6}$ CO$_2$H, (4) (CH2)$_{1-6}$CONHR wherein R is C$_{1-6}$alkyl, optionally branched; aryl which is phenyl optionally substituted by one or more of lower alkyl of from one to four carbons, halogen wherein halogen is fluoro, chloro, bromo, or iodo, trifluoromethyl, cyano, carboxy, alkoxycarbonyl wherein the alkoxy is of from one to four carbons, alkylthio wherein the alkyl is of from one to four carbons, nitro, acyl of from two to four carbons, hydroxy, $C_{1-6}$-alkoxy, $CH_2CO_2R'$ wherein $R'$ is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, optionally branched; aralkyl which is aryl as defined above attached through $C_{1-4}$alkyl;

$R^5$ is $NO_2$, F, $CF_3$, $SO_2NR''R'''$ wherein $R''$ and $R'''$ independently are hydrogen or $C_{1-6}$-alkyl, or CN; and $R^4$, $R^6$, $R^7$ independently are hydrogen, $C_{1-6}$-alkyl which may be branched, phenyl, halogen, $C_{1-6}$-alkoxy, $NO_2$, $SO_2NR''R'''$ wherein $R''$ and $R'''$ independently are hydrogen or $C_{1-6}$-alkyl, CN, or $CF_3$, or $R^6$ and $R^7$ together form an additional 4- to 7-membered ring which may be aromatic or partially saturated and which may be substituted with halogen, $NO_2$, $CF_3$, CN, $SO_2NR''R'''$ wherein $R''$ and $R'''$ independently are hydrogen or $C_{1-6}$-alkyl, and $R^4$ has the meaning set forth above; and that $R^5$ is different from $NO_2$ and F when $R^1$, $R^4$, $R^6$, and $R^7$ are not other than hydrogen and $R^2$ is not other than hydrogen or benzyl; and that $R^5$ is different from $NO_2$, when $R^1$, $R^2$, $R^4$, and $R^6$ are not other than hydrogen and $R^7$ is not other than $NO_2$, comprising the step of reacting a compound of the formula

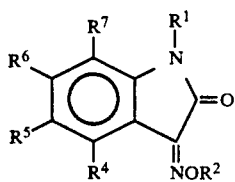

wherein
$R^1$, $R^4$, $R^5$, $R^6$, and have the meanings set forth above, with a compound having the formula $NH_2OR^2$, wherein $R^2$ has the meaning set forth above, and moreover the use of a compound having the formula

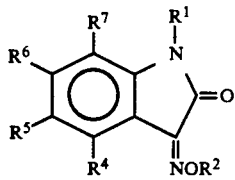

wherein
$R^1$ is hydrogen, $C_{1-6}$-alkyl which may be branched, $C_{3-7}$-cycloalkyl, benzyl, phenyl which may be substituted, acyl, hydroxy, $C_{1-6}$-alkoxy, $CH_2CO_2R'$ wherein $R'$ is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, or $CH_2C(=NOH)NH_2$;

$R^2$ is (1) alkenyl of from two to six carbon atoms, preferably allyl, (2) alkynyl of from two to six carbons, preferably propargyl, (3) $(CH_2)_{1-6}CO_2H$, (4) $(CH_2)_{1-6}CONHR$ wherein R is $C_{1-6}$alkyl, optionally branched; aryl which is phenyl optionally substituted by one or more of lower alkyl of from one to four carbons, halogen wherein halogen is fluoro, chloro, bromo, or iodo, trifluoromethyl, cyano, carboxy, alkoxycarbonyl wherein the alkoxy is of from one to four carbons, alkylthio wherein the alkyl is of from one to four carbons, nitro, acyl of from two to four carbons, hydroxy, $C_{1-6}$-alkoxy, $CH_2CO_2R'$ wherein $R'$ is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, optionally branched; aralkyl which is aryl as defined above attached through $C_{1-4}$alkyl;

$R^4$, $R^5$, $R^6$, $R^7$ independently are hydrogen $C_{1-6}$-alkyl which may be branched, phenyl, halogen, $C_{1-6}$-alkoxy, $NO_2$, CN, $SO_2NR''R'''$ wherein $R''$ and $R'''$ independently are hydrogen or $C_{1-6}$-alkyl, or $CF_3$; or $R^6$ and together form an additional 4 to 7 membered ring which may be aromatic or partial saturated and which may be substituted with halogen, $NO_2$, $CF_3$, CN, $SO_2NR''R'''$ wherein $R'''$and $R'''$independently are hydrogen or $C_{1-6}$-alkyl, and $R^4$ and $R^5$ have the meanings set forth above, for the preparation of a medicament useful in the treatment of conditions sensitive to an excitatory amino acid, and the use as above wherein at least one of $R^4$, $R^5$, $R^6$, or is an electron withdrawing substituent such as $NO_2$, $CF_3$, CN, $SO_2NR''R'''$, or halogen and $R^1$, $R^2$, $R^4$, $R^5$, $R^6$, $R''$ and $R'''$ otherwise have the meanings set forth above, and further a method of preparing a pharmaceutical preparation containing an active ingredient s active ingredient an effective amount of a compound having the formula

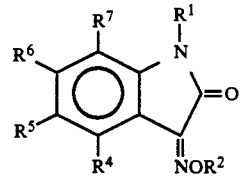

wherein
$R^1$ is hydrogen, $C_{1-6}$-alkyl which may be branched, $C_{3-7}$-cycloalkyl, benzyl, phenyl which may be substituted, acyl, hydroxy, $C_{1-6}$-alkoxy, $CH_2CO_2R'$ wherein $R'$ is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, or $CH_2C(=NOH)NH_2$;

$R^2$ is (1) alkenyl of from two to six carbon atoms, preferably allyl, (2) alkynyl of from two to six carbons, preferably propargyl, (3) $(CH_2)_{1-6}CO_2H$, (4) $(CH_2)_{1-6}CONHR$ wherein R is $C_{1-6}$alkyl, optionally branched; aryl which is phenyl optionally substituted by one or more of lower alkyl of from one to four carbons, halogen wherein halogen is fluoro, chloro, bromo, or iodo, trifluoromethyl, cyano, carboxy, alkoxycarbonyl wherein the alkoxy is of from one to four carbons, alkylthio wherein the alkyl is of from one to four carbons, nitro, acyl of from two to four carbons, hydroxy, $C_{1-6}$-alkoxy, $CH_2CO_2R'$ wherein $R'$ is hydrogen or $C_{1-6}$-alkyl which may be branched, $CH_2CN$, $CH_2CON$-

$R^{IV}R^V$ wherein $R^{IV}$ and $R^V$ independently are hydrogen or $C_{1-6}$-alkyl, optionally branched; aralkyl which is aryl as defined above attached through $C_{1-4}$alkyl;

$R^4$, $R^5$, $R^6$, $R^7$ independently are hydrogen, $C_{1-6}$-alkyl which may be branched, phenyl, halogen, $C_{1-6}$-alkoxy, $NO_2$, $CN$, $SO_2NR''R'''$ wherein $R''$ and $R'''$ independently are hydrogen or $C_{1-6}$-alkyl, or $CF_3$; or $R^6$ and together form an additional 4 to 7 membered ring which may be aromatic or partial saturated and which may be substituted with halogen, $NO_2$, $CF_3$, $CN$, $SO_2NR''R'''$ wherein $R''$ and $R'''$ independently are hydrogen or $C_{1-6}$-alkyl, and $R^4$ and $R^5$ have the meanings set forth above.

With respect to $R^2$ the preferred substituents are $(CH_2)_{1-3}CO_2H$; $(CH_2)_{1-3}CONHR$, ($R_{10}$ as defined above).

The more preferred substituents are $CH_2CO_2H$; $CH_2CONHR$ wherein R is $CH_3$, $CH_2Ph$, $Ph$, $SO_2R^{10}$.

The still more preferred compounds have the following $R^2$ substituents: $CH_2CO_2H$, $CH_2CONHSO_2R^{10}$.

The most preferred compounds are:
4,6-dichloro-1H-indole-2,3 dione-3-(0-carboxymethyloxime),
4,6-dichloro-1H indole-2,3-dione-3-(O-methylsulphonamidocarboxymethyloxime),
4,6-dichloro-1H-indole-2,3-dione-3-(O-phenylsulphonamidocarboxymethyloxime),
5,6-dichloro-1H-indole-2,3-dione-3-(O-carboxylmethyloxime),
5,6-dichloro 1H-indole-2,3-dione-3-(O-methylsulphonamidocarboxymethyloxime),
5,6-dichloro-1H-indole-2,3-dione-3-(O-phenylsulphonamidocarooxymetnyloxime),
4,6-dinitro-1H-indole-2,3-dione-3-(O-carboxymethyloxime),
4,6 dinitro-1H-indole-2,3-dione-3-(O-methylsulphonamidomethyloxime),
4,6-dinitro 1H indole-2,3 dione-3-(O-phenylsulphonamidocarboxymethyloxime),
5,6-dinitro-1H-indole-2,3-dione 3-(O-carboxymethyloxime),
5,6-dinitro IH indole 2,3 dione 3 (O-methylsulphonamidocarboxymethyloxime),
5,6 dinitro-1H-indole 2,3-dione-3-(O-phenylsulphonamidocarboxymethyloxime.

The compounds of the present invention contain asymmetric carbon atoms. The instant invention includes the individual diastereomers and enantiomers, which may be prepared or isolated by methods known to those skilled in the art.

Oximes can exist also as syn and anti forms, both are included in the present invention.

Any resulting racemate can be resolved into the optical antipodes by known methods, for example, by separation of the diasteromeric salts thereof, with an optically active acid, and liberating the optically active amine compound by treatment with a base. Racemic compounds of the present invention can thus be resolved into their optical antipodes, e.g., by fractional crystallization of d- or l-(tartarates, mandelates, or camphorsulfonate) salts. The compounds of the instant invention may also be resolved by the formation of diastereomeric amides by reaction of the compounds of the instant invention with an optically active activated carboxylic acid such as that derived from (+) or (−) phenylalanine, (+) or (−) phenylglycine, (+) or (-)-camphanic acid or by the formation of diastereomeric carbamates by reaction of the compounds of the instant invention with an optically active chloroformate or the like.

Additional methods for resolving optical isomers, known to those skilled in the art may be used, for example, those discussed by J. Jaques, A. Collet, and S. Wilen in *Enantiomers, Racemates, and Resolutions*, John Wiley and Sons, New York (1981).

BIOLOGICAL ACTIVITY

The compounds of the invention exhibit valuable biological properties because of their strong excitatory amino acid (EAA) (glycine, glutamate, quisqualate, ATPA, AMPA, kainate, NMDA) antagonizing properties.

For example compounds of the invention exhibit strong pharmacological in vivo ATPA and quisqualate antagonizing effects demonstrating their utility as novel orally-bioavailable excitatory amino acid antagonists, which makes them useful in the treatment of, for example, excitatory amino acid dependent psychosis, excitatory amino dependent anoxia, excitatory amino acid dependent ischemia, excitatory amino acid dependent convulsions, and excitatory amino acid dependent migraine.

Compounds of the invention will inhibit ATPA-induced rigidity and quisqualate or NMDA-induced convulsions with an $ED_{50}$ in the range of 0.1–10.0 mg/kg.

Compounds of the invention show potent in vitro affinity for the glutamate subreceptors kainate, quisqualate, and glycine receptors. These properties make the compounds useful in the treatment of human malfunctions related to the excitatory amino acids (EAA).

BIOLOGICAL TESTING

The above-mentioned tests are performed as described in more detail below and are based upon the principles also described hereinafter.

ATPA-induced rigidity

The selective quisqualate receptor agonist ATPA induces rigidity in female NMRI mice at doses between 3 to 15 mg/kg and clonic-tonic seizures and death, probably due to respiratory arrest, at doses between 15 and 40 mg/kg after intravenous (IV) administration.

METHOD

ATPA (RS)-α-amino-3-hydroxy-5tert-butyl-4-isoxazolepropionic acid) was dissolved in distilled water and test compound was dissolved in a polyoxyl 40 hydrogenated castor oil (5% Cremorphor RH ™ (BASF)).

Test compound was administered either IV 5, 30, or 120 minutes before or PO 30 minutes before an IV administration of 15 mg/kg of ATPA to eight female NMRI mice per dose and the number of mice experiencing rigidity 5 minutes later was noted. An $ED_{50}$ value was calculated from at least three doses of test compound as the dose inhibiting 50% of the mice from having rigidity.

Quisqualate-induced clonic seizures

Quisqualate given ICV (intracerebroventricular) to DBA/2 mice induces clonic seizures which can be inhibited by both NMDA and non-NMDA receptor antagonists after IV administration.

METHOD

Test compound was given IV 5 minutes before a 20 ∞g ICV administration of quisqualate to ten male DBA/2 mice (weighing 10–12 g) per dose. The number of mice experiencing clonic seizures within the next 2 minutes was noted. An $ED_{50}$ value was calculated as the dose inhibiting 50% of the mice from having clonic seizures.

NMDA-induced clonic seizures

NMDA given ICV to NMRI mice induces clonic seizures which can be inhibited by NMDA receptor antagonists.

METHOD

Test compound was given IV 5 minutes before a 0.5 μg ICV administration of NMDA to ten male NMRA mice per dose. The number of mice experiencing clonic seizures within the next 2 minutes were noted. An $ED_{50}$ value was calculated as the dose inhibiting 50% of the mice from having clonic seizures.

COCAINE-INDUCED HYPERMOBILITY

Quisqualate and kainate administered locally induce an increase in dopamine release in nucleus accumbens and nucleus caudatus accompanied by stereotype behavior such as hyperlocomotion, rearing, sniffing, and grooming. These effects can be inhibited by selective quisqualate antagonists administered locally by the microdialysis method.

Also the dopamine uptake inhibitor cocaine administered SC induced hypermotility which can be inhibited by administration of the glutamate antagonist GDEE into nucleus accumbens.

For these reason (and others) it has been concluded that non-NMDA receptors regulate the release of dopamine in nucleus accumbens and that non-NMDA receptor antagonists can alleviate the symptoms of psychosis.

Method

Test compound was administered orally at doses of 0.1, 1, 10, and 30 mg/kg 30 minutes before the administration of 25 mg/kg cocaine IP to female NMRI mice and the locomotor activity of two mice per box was measured for the next 2 hours by use of eight infrared photobeams per box. The mice had been adapted to he box for at least 16 hours to avoid exploratory motility (neophobia).

The quisqualate binding assay was performed as described by T. Honore, et al, Neuroscience Letters 1985;54:57–32.

The kainate binding assay was performed as described by T. Honore, et al, Neuroscience Letters 1986;65:47–52.

The glycine binding assay was performed as described by W. Frost White, et al, Journal of Neurochemistry 1989;53(2):503–12.

PHARMACEUTICAL COMPOSITIONS

The compounds of the invention, together with a conventional adjuvant, carrier, or diluent, may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories, for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Tablets containing ten (10) mg of active ingredients or, more broadly, 0.1 to 100 mg, per tablets are accordingly suitable representative unit dosage forms.

Solid forms of pharmaceutical compositions for PO administration and injectable solutions are preferred.

METHOD OF TREATING

The compounds of this invention are extremely useful in the treatment of central nervous system disorders related to their biological activity. The compounds of this invention may accordingly be administered to a subject, including a human, in need of treatment, alleviation, or elimination of an indication associated with the biological activity of the compounds. This includes especially excitatory amino acid dependent psychosis, excitatory amino acid dependent anoxia, excitatory amino acid dependent ischemia, excitatory amino acid dependent convulsions and excitatory amino acid dependent migraine. Suitable dosage ranges are 0.1 to 1000 mg daily, 10 to 400 mg daily, and especially 30 to 100 mg daily, dependent as usual upon the exact mode of administration, for in which administered, the indication toward which the administration is directed, the subject involved and the body weight of the subject involved, and further the preference and experience of the physician or veterinarian in charge.

CHEMICAL EXAMPLES

Some compounds of the invention are old, and others are novel chemical entities. In any way the compounds of the invention may be prepared according to chemical methods which are well known.

EXAMPLE 1 a) 1-phenyl-1H-indole-2,3-dione.

To a stirred solution of diphenylamine (3.2 g, 20 mmol) and 4-dimethylaminopyridine (10 mg) in chloroform (50 mL) was dropwise added oxalychloride (3 mL) The resulting mixture was refluxed for 5 hours, whereafter it was cooled to room temperature and evaporated in vacuo.

The residue (oil) was redissolved in methylene chloride (50 mL) and dry $AlCl_3$ (3 g) was added. Stirring at room temperature was continued for 30 hours, whereafter ethanol (10 mL) followed by water (100 mL) were added. The organic phase was washed with saturated $Na_2CO_3$, dried over $Na_2SO_4$ and evaporated. The crystalline residue was stirred in ether (40 mL) and the product was filtered off. Yield: 2.65 g orange crystals, m.p. 139–141° C., litt. 138° C.

b) The following 1H-indole-2,3-diones were prepared according to known literature procedures.

1) Organic Synthesis Col Vol. I p. 327.

2) Martinet J. Compt Rend 1918;166:851.

4,6-ditrifluoromethyl-1H-indole-2,3-dione[1]), m.p. 162° to 165° C.

1H-benz[g]indole-2,3-dione-[2]), m.p. 242° to 245° C.

7-trifluoromethyl-1H-indole-2,3-dione[1]), m.p. 181° to 183° C.

1H-6,7,8,9-tetrahydro-benz[g]indole-2,3-dione, m.p. 224° to 226° C.

6-methoxy-1H-indole-2,3-dione, m.p. >310° C. 7-trifluoromethyl-1H-indole-2,3-dione, m.p. 180° to 184° C.

c) 1-methyl-5-nitro-7-trifluoromethyl-1H-indole-2,3-dione.

To a stirred 10° C. warm solution of $KNO_3$ (0.5 g) in 10 mL of conc. $H_2SO_4$ was dropwise added to a solution of 1-methyl-7-trifluoromethyl-1H-indole-2,3-dione in 10 mL of conc. $H_2SO_4$. The addition was completed after 10 minutes, whereafter stirring was continued for 15 minutes at room temperature. The reaction mixture was poured on ice whereby the title compound precipitated as yellow crystals. The crystals were collected by filtration and washed with water. m.p. 168° to 169° C.

In a similar manner to c), the following nitro compounds were prepared:

5-nitro-1H-6,7,8,9-tetrahydro-benz[g]indole-2,3-dione, m.p. 232° to 236° C.

5-nitro-1-methyl-1H-benz[g]indole-2,3-dione, m.p. 255° to 258° C.

d) 5,7-dinitro-1-methyl-1H-indole-2,3-dione.

To a stirred solution of 5,7-dinitro-1H-indole-2,3-dione (1.2 g) in dry dimethylformamide (20 mL) was added sodium hydride (0.24 g 55% in mineral oil). After the hydrogen evolution had ceased methyl iodide (0.37 mL) was added. Stirring at room temperature was continued for 2 hours, whereafter the crude product was precipitated as an oil by addition of water (100 mL) to the reaction mixture. The oil crystallized upon treatment with ether/pentane, m.p. 154° to 157° C.

In a similar manner to d), the following 1-alkyl or 1-benzyl-1H-indole-2,3-diones were prepared.

5,7dinitro-1-ethyl-1H-indole-2,3-dione, m.p. 135° to 140° C.

5-bromo-1-methyl-1H-indole-2,3-dione, m.p. 157° to 160° C.

1H-1-methyl-6,7,8,9-tetrahydro-benz[g]indole-2,3-dione, m.p. 157° to 160° C.

5,7-dibromo-1-methyl-1H-indole-2,3-dione, m.p. 170° to 173° C.

5,6-dichloro-1-methyl-1H-indole-2,3-dione, m.p. 180° to 184° C.

4,5-dichloro-1-methyl-1H-indole-2,3-dione, m.p. 237° to 239° C.

1-methyl-5-nitro-1H-indole-2,3-dione, m.p. 196° to 199° C.

1-benzyl-5,7dinitro-1H-indole-2,3-dione, m.p. 127° to 131° C.

4,6-ditrifluoromethyl-1-methyl-1H-indole, m.p. 93° to 94° C.

1-methyl-7trifluoromethyl-1H-indole-2,3-dione, m.p. 120° to 122° X.

6methoxy-1methyl-1H-indole-2,3-dione, m.p. 175° to 178° C.

5.7-dinitro-1-(ethoxycarbonylmethyl)-1H-indole-2,3-dione, (oil).

1-methyl-1H-benz[g]indole-2,3dione, m.p. 122° to 126° C.

1-(ethoxycarbonylmethyl)-1H-indole-2,3-dione, m.p. 97° to 102° C.

5,7-dibromo-1-(ethoxycarbonylmethyl)-1H-indole-2,3-dione, m.p. 97° to 102° C.

1-methyl-1H-6,7,8,9-etrahydrobenz[g]indole-2,3-dione, m.p. 160° to 165° C.

EXAMPLE 2

O-substituted hydroxyamines and O-carboxyalkylhydroxylamines are reacted with a substrate, 1H-indole-2,3-dione in the following manner to give the target oxime derivatives. The starting indole-2,3-dione, hydroxylamine hydrochloride and sodium carbonate are stirred at room temperature in ethanol for 1 hour, whereafter acetic acid followed by water are added. The mixture is cooled on ice and the crystalline product is obtained by filtration. The resulting substituted 1H-indole-2,3-dione-3-(O-substituted oxime) is further derivatized by activation of the free carboxylic acid with carboxyldiimidazole or the like followed by reaction with an amine, or activated sulphonamide group (activation of the sulphonamide group is achieved by the addition of a suitable base, for example, diazobicycloundecane (DBU) or sodium hydride in a suitable solvent such as THF or DMF.

1) A. Reiszert, Ber. Vol. 41, 3921.

EXAMPLE 3 a) 1-carboxymethyl-1H-indole-2,3dione.

8.39 g (36 mmol) 1-(ethoxycarbonylmethyl)-1H-indole-2,3-dione and 4N NaOH (10 mL, 40 mmol) were dissolved in 30 mL $H_2O$ and 10 mL absolute ethanol and the mixture was heated at reflux for 30 minutes. The reaction mixture was cooled and added excess hydrochloric acid. The precipitate was isolated. Yield of title compound is 6.2 g.

b) 1-chlorocarbonylmethyl-1H-indole-2,3-dione.

1 g of the product prepared under a) was suspended in toluene (10 mL) and $SOCl_2$ (1.0 mL, 13.78 mmol) was added. The mixture was stirred at RT for 2 hours and additionally at 70° C. for 30 minutes and thereafter at reflux for 1 hour. The reaction mixture was stirred at RT overnight whereafter the precipitated yellow crystals were isolated and washed with toluene. Yield of title compound was 1.3 g. including solvent content.

c) 1-aminocarbonylmethyl-1H-indole-2,3-dione.

The product prepared under b) was dissolved in dry THF (50 mL) and to the solution was added liquid $NH_3$. The resulting mixture was stirred overnight at RT. The precipitated orange crystals were isolated and were washed with water. Yield of title compound was 0.46 g.

d) 1-cyanomethyl-1H-indole-2,3-dione.

Triphenylphosphine (0.75 g, 2.84 mmol) was dissolved in methylenechloride and to the solution was added dropwise to $Br_2$ (0.15 mL, 2.84 mmol) in methylenechloride (20 mL). To this mixture the product prepared under c) was added, and thereafter triethylamine (0.8 mLO, 5.68 mmol) was added dropwise. The mixture was stirred for 30 minutes. The reaction mixture was evaporated in vacuo and the residue was taken up in ether. The precipitate from this mixture was filtered off and the ether solution was washed with water and dried ($MgSO_4$). The ether solution was evaporated in vacuo and the residue was washed with isopropanol. Yield of title compound was 0.11 g. m.p. 125° to 128° C.

e) 1-(acetamideoxime-2-yl)-1H-indole-2,3-dione-3-oxime.

The product prepared under d) (90 mg, 0.48 mmol), hydroxylamine hydrochloride (70 mg, 1.06 mmol) and potassium carbonate (150 mg, 1.06 mmol) and methanol (10 mL) were mixed and the mixture was stirred in RT overnight. The reaction mixture was evaporated in vacuo. The residue was washed with water containing small amounts of acetic acid. Yield of title compound was 70 mg. m.p. 227° to 229° C.

It is thus seen that the present invention provides a new and convenient process for the production of indole-2,3-dione-3-oxime compounds, certain novel indole-2,3-dione-3-oxime compounds which are useful as excitatory amino acid antagonists, pharmaceutical-compositions useful as excitatory amino acid antagonists comprising certain indole-2,3-dione-3-oxime compounds, and a method of antagonizing the biological effects of excitatory amino acids in a subject in need thereof comprising the step of administering certain indole-2,3-dione-3-oxime compounds of a pharmaceutical composition comprising the same together with a pharmaceutically acceptable diluent or carrier, all having the foregoing characteristics and advantages.

It is to be understood that the invention is not to be limited to the exact details of operation, or to the exact methods, procedures, or embodiments shown and described, as obvious modifications and equivalents will be apparent to one skilled in the art, and the invention is therefore to be limited only by the full scope of the appended claims.

I claim:

1. A method of antagonizing the biological effects of an excitatory amino acid of a subject in need of such antagonization comprising the step of administering to said subject an effective excitatory amino acid antagonizing amount of an indole-2,3-dione-3-oxime compound having the formula

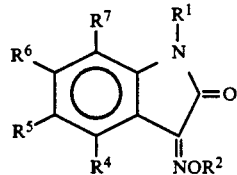

and isomers thereof wherein $R^1$ is hydrogen, $C_{1-6}$-alkyl which may be branched, $C_{3-7}$-cycloalkyl, benzyl, phenyl which may be substituted, acyl, hydroxy, $C_{1-6}$-alkoxy, $CH_2CO_2R'$ wherein R' is hydrogen or $C_{1-6}$alkyl which may be branched, $CH_2CN$, $CH_2CONR^{IV}R^V$ wherein $R^{IV}$ and $R^V$ independently are hydrogen or $C_{1-6}$alkyl, or $CH_2C(=NOH)NH_2$;

$R^2$ is (1) alkenyl of from two to six carbon atoms, (2) of from two to six carbons, (3) $(CH_2)_{1-6}CO_2H$, (4) $(CH_2)_{1-6}CONHR$ wherein R is $C_{1-6}$alkyl, optionally branched; aryl which is phenyl optionally substituted by one or more of lower alkyl of from one to four carbons, halogen trifluoromethyl, cyano, carboxy, alkoxycarbonyl wherein the alkoxy is of from one to four carbons, alkylthio wherein the alkyl is of from one to four carbons, nitro, acyl of from two to four carbons, hydroxy, $C_{1-6}$-alkoxy, $CH_2CO_2R'$ wherein R' is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, optionally branched; aralkyl which is aryl as defined above attached through $C_{1-4}$alkyl; or $SO_2R^{10}$ wherein $R^{10}$ is $C_{1-12}$alkyl, optionally branched; aryl which is phenyl optionally substituted by ne or more of lower alkyl of from one to four carbons, halogen trifluoromethyl, cyano, $NH_2$, $NHR^{11}$ wherein $R^{11}$ is $C_{1-4}$alkyl, $NHCOR^{11}$ wherein $R^{11}$ is as defined above, carboxy, alkoxycarbonyl wherein the alkoxy is of from one to four carbons, alkylthio wherein the alkyl is of from one to four carbons, nitro, acyl of from two to four carbons, hydroxy, $C_{1-6}$-alkoxy, $CH_2CO_2R'$ wherein R' is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, optionally branched; aralkyl which is aryl as defined above attached through $C_{1-4}$alkyl; $R^4R^5$, $R^6$, $R^7$ independently are hydrogen, $C_{1-6}$-alkyl which may be branched, phenyl, halogen, $C_{1-6}$-alkoxy, $NO_2$, CN, $CF_3$, or $SO_2NR''R'''$ wherein R'' and R''' independently are hydrogen or $C_{1-6}$-alkyl; or $R^6$ and $R^7$ together form an additional 4- to 7-membered ring which may be aromatic or partial saturated and which may be substituted with halogen, $NO_2$, $CF_3CN$, $SO_2NR''R'''$ wherein R'' and R''' independently are hydrogen or $C_{1-6}$-alkyl, and $R^4$ and $R^5$ have the meanings set forth above.

2. A method according to claim 1 wherein at least one of $R^4$, $R^5$, $R^6$, or $R^7$ is an electron withdrawing substituent such as selected from the group consisting of halogen and $R^1$, $R^2$, $R^4$, $R^5$, $R^6$, $R^7$, R'', and R''' otherwise have the meanings set forth in claim 1.

3. A method according to claim 1 wherein $R^5$ is $NO_2$, F, $CF_3$, or CN.

4. A method of antagonizing the biological effects of an excitatory amino acid according claim 1, wherein the compound is administered in the form of a pharmaceutical composition thereof, in which it is present together with a pharmaceutically acceptable carrier or diluent.

5. A method of antagonizing the biological effects of an excitatory amino acid according claim 2, wherein the compound is administered in the form of a pharmaceutical composition thereof, in which it is present together with a pharmaceutically acceptable carrier or diluent.

6. A pharmaceutical composition for use in antagonizing the biological effects of an excitatory amino acid of a subject in need of such antagonizing comprising an effective excitatory amino acid antagonizing amount of a compound having the formula

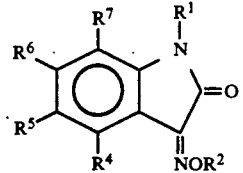

and isomers thereof;

$R^1$ as defined in claim 1.

$R^2$ is (1) alkenyl of from two to six carbon atoms, (2)alkynyl of from two to six carbons, (3) $(CH_2)_{1-6}CO_2H$, (4) $(CH_2)_{1-6}CONHR$ wherein R is $C_{1-6}$alkyl, optionally branched; aryl which is phenyl optionally substituted by one or more of lower alkyl of from one to four carbons, halogen, wherein halogen is fluoro, chloro, bromo, or iodo, trifluoromethyl, cyano, carboxy, alkoxycarbonyl wherein the alkoxy is of from one to four carbons, alkylthio wherein the aklyl is of from one to four carbons, nitro, acyl of from two to four carbons, hydroxy, $C_{1-6}$-alkyl $CH_2CO_2R'$ wherein R' is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, optionally branched; aralkyl which is aryl as defined above attached through $C_{1-4}$alkyl; or $SO_2R^{10}$ wherein $R^{10}$ is $C_{1-2}$alkyl, optionally branched; aryl which is phenyl optionally substituted by one or more of lower aklyl of from one to four carbons, halogen trifluoromethyl, cyano, $NH_2$, $NHR^{11}$ wherein $R^{11}$ is $C_{1-4}$akyl, $NHCOR^{11}$ wherein $R^{11}$ is as defined above, carboxy, alkoxycarbonyl wherein the alkoxy is of from one to four carbons, alkylthio wherein the alkyl is of from one to four carbons, nitro, acyl of from two to four carbons, hydroxy, $C_{1-6}$-alkoxy, $CH_2CO_2R'$ wherein $R'$ is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, optionally branched; aralkyl which is aryl as defined above attached through $C_{1-4}$alkyl; $R^4$, $R^5$, $R^6$, $R^7$ independently are hydrogen, $C_{1-6}$-alkyl which may be branched, phenyl, halogen, $C_{1-6}$-alkoxy, $NO_2$, CN, $SO_2NR''R'''$ wherein $R''$ and $R'''$ independently are hydrogen or $C_{1-6}$-alkyl, or $CF_3$, or $R^6$ and $R^7$ together form an additional 4 to 7 membered ring which may be aromatic or partial saturated and which may be substituted with halogen, $NO_2$, $CF_3$, CN, $SO_2NR''R'''$ wherein $R''$ and $R'''$ independently are hydrogen or $C_{1-6}$-alkyl, and $R^4$ and $R^5$ have the meanings set forth above, at least one of $R^4$, $R^6$, and $R^7$ are other than hydrogen when $R^5$ is H, Cl, or Br; or $R^1$ is $C_{1-6}$alkyl which may be branched, $C_{3-7}$-cycloalkyl, benzyl, phenyl which may be substituted, acyl, hydroxy, $C_{1-6}$-alkoxy, $CH_2CO_2R'$ wherein $R'$ is hydrogen or $C_{1-6}$alkyl which may be branched, $CH_2CN$, $CH_2CONR^{IV}R^V$ wherein $R^{IV}$ and $R^V$ independently are hydrogen or $C_{1-6}$-alkyl, $CH_2C(=NOH)NH_2$; or $R^2$ is (1) alkenyl of from two to six carbon atoms, (2) alkynyl of from two to six carbons, (3) $(CH_2)_{1-6}$ $(CO_2H$, (4) $(CH_2)_{1-6}CONHR$ wherein R is $C_{1-6}$alkyl, optionally branched; aryl which is phenyl optionally substituted by one or more of lower alkyl of from one to four carbons, halogen, trifluoromethyl, cyano, carboxy, alkoxycarbonyl wherein the alkoxy is of from one to four carbons, alkylthio wherein the alkyl is of from one to four carbons, nitro, acyl of from two to four carbons, hydroxy, $C_{1-6}$-alkoxy, $CH_2CO_2R'$ wherein $R'$ is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, optionally branched; aralkyl which is aryl as defined above attached through $C_{1-4}$alkyl; of $SO_2R^{10}$ wherein $R^{10}$ is $C_{1-12}$alkyl, optionally branched; aryl which is phenyl optionally substituted by one or more of lower alkyl of from one to four carbons, halogen, trifluoromethyl, cyano, $NH_2$, $NHR^{11}$ wherein $R^{11}$ is $C_{1-4}$alkyl, $NHCOR^{11}$ wherein $R^{11}$ is as defined above, carboxy, alkoxycarbonyl wherein the alkoxy is of from one to four carbons, alkylthio wherein the alkyl is of from one to four carbons, nitro, acyl of from two to four carbons, hydroxy, $C_{1-6}$-alkoxy, $CH_2CO_2R'$ wherein $R'$ is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, optionally branched; aralkyl which is aryl as defined above attached through $C_{1-4}$alkyl; $R^4$, $R^5$, $R^6$, $R^7$ independently are hydrogen, $C_{1-6}$-alkyl which may be branched, phenyl, halogen, $C_{1-6}$-alkoxy, $NO_2$, CN, $SO_2NR''R'''$ wherein $R''$ and $R'''$ independently are hydrogen or $C_{1-6}$-alkyl, or $CF_3$, or $R^6$ and $R^7$ together form an additional 4 to 7 membered ring which may be aromatic or partial saturated and which may be substituted with halogen, $NO_2$, $CF_3$, CN, $SO_2NR''R'''$ wherein $R''$ and $R'''$ independently are hydrogen or $C_{1-6}$-alkyl, and $R^4$ and $R^5$ have the meanings set forth above, at least one of $R^4$, $R^5$, $R^6$, $R^7$ are other than hydrogen when $R^1$ is methyl, at least one of $R^4$ and $R^5$ are other than hydrogen when $R^1$ is phenyl which may be substituted, and at least one of $R^4$ and $R^5$ are other than hydrogen when $R^6$ and $R^7$ together form an additional benzene ring.

7. A method of antagonizing the biological effects of an excitatory amino acid of a subject in need thereof comprising the step of administering to said subject a pharmaceutical composition according to claim 6.

8. A compound having the formula

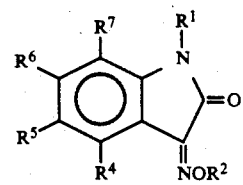

and isomers thereof wherein $R^1$ is $C_{1-6}$-alkyl which may be branched, $C_{3-7}$-cycloalkyl benzyl, phenyl which may be substituted, acyl, hydroxy, $C_{1-6}$-alkoxy, $CH_2CO_2R'$ wherein $R'$ is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, or $CH_2C(=NOH)NH_2$;

$R^2$ is (1) alkenyl of from two to six carbon atoms, (2) alkynyl of from two to six carbons, (3) $(CH_2)_{1-6}$ $CO_2H$, (4) $(CH_{2 1-6}CONHR$ wherein R is $C_{1-6}$alkyl, optionally branched; aryl which is phenyl optionally substituted by one or more of lower alkyl of from one to four carbons, halogen trifluoromethyl, cyano, carboxy, alkoxycarbonyl wherein the alkoxy is of from one to four carbons, alkylthio wherein the alkyl is of from one to four carbons, nitro, acyl of from two to four carbons, hydroxy, $C_{1-6}$-alkoxy, $CH_2CO_2R'$ wherein $R'$ is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, optionally branched; aralkyl which is aryl as defined above attached through $C_{1-4}$alkyl; or $SO_2R^{10}$ wherein $R^{10}$ is $C_{1-12}$alkyl, optionally branched; aryl which is phenyl optionally substituted by one or more of lower alkyl of from one to four carbons, halogen trifluoromethyl, cyano, $NH_2$, $NHR^{11}$ wherein $R^{11}$ is $C_{1-4}$alkyl, $NHCOR^{11}$ wherein $R^{11}$ is as defined above, carboxy, alkoxycarbonyl wherein the alkoxy is of from one to four carbons, alkylthio wherein the alkyl is of from one to four carbons, nitro, acyl of from two to four carbons, hydroxy, $C_{1-6}$-alkoxy $CH_2CO_2R'$ wherein $R'$ is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, optionally branched; aralkyl which is aryl as defined above attached through $C_{1-4}$alkyl; $R^5$ is $NO_2$, F, $CF_3$, SO$_2$NR''R''' wherein R'' and R''' independently are hydrogen or C$_{1-6}$-alkyl, or CN; and R$^4$, R$^6$, R$^7$ independently are hydrogen, C$_{1-6}$-alkyl which may be branched, phenyl, halogen, C$_{1-6}$-alkoxy, NO$_2$, CN, SO$_2$NR''R''' wherein R'' and R''' independently are hydrogen or C$_{1-6}$-alkyl, or CF$_3$, or R$^6$ and R$^7$ together form an additional 4 to 7 membered ring which may be aromatic or partial saturated and which may be substituted with halogen, NO$_2$, CF$_3$, CN, SO$_2$NR''R''' wherein R'' and R''' independently are hydrogen or C$_{1-6}$-alkyl, or CF$_3$, or R$^6$ and R$^7$ together form an additional 4 to 7 membered ring which may be aromatic or partial saturated and which may be substituted with halogen, NO$_2$, CF$_3$, CN, SO$_2$NR''R''' wherein R'' and R''' independently are hydrogen or C$_{1-6}$-alkyl, and R$^4$ has the meaning set forth above.

9. A compound having the formula

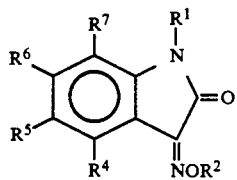

and isomers thereof wherein R$^1$ is C$_{1-6}$-alkyl which may be branched, C$_{3-7}$-cycloalkyl, benzyl, acyl, hydroxy, C$_{1-6}$-alkoxy, CH$_2$CO$_2$R' wherein R' is hydrogen or C$_{1-6}$-alkyl which may be branched, CH$_2$CN, CH$_2$CONR$^{IV}$R$^V$ wherein R$^{IV}$ and R$^V$ independently are hydrogen or C$_{1-6}$-alkyl, or CH$_2$C(=NOH)NH$_2$;

R$^2$ is (1) alkenyl of from two to six carbon atoms, (2) alkynyl of from two to six carbons, (3) (CH$_2$)$_{1-6}$CO$_2$H, (4) (CH$_2$)$_{1-4}$CONHR wherein R is C$_{1-6}$alkyl, optionally branched; aryl which is phenyl optionally substituted by one or more of lower alkyl of from one to four carbons, halogen trifluoromethyl, cyano, carboxy, alkoxycarbonyl wherein the alkoxy is of from one to four carbons, alkylthio wherein the alkyl is of from one to four carbons, nitro, acyl of from two to four carbons, hydroxy, C$_{1-6}$-alkoxy, CH$_2$CO$_2$R' wherein R' is hydrogen or C$_{1-6}$-alkyl which may be branched, CH$_2$CN, CH$_2$CONR$^{IV}$R$^V$ wherein R$^{IV}$ and R$^V$ independently are hydrogen or C$_{1-6}$-alkyl, optionally branched; aralkyl which is aryl as defined above attached through C$_{1-4}$alkyl; or SO$_2$R$^{10}$ wherein R$^{10}$ is C$_{1-12}$alkyl, optionally branched; aryl which is phenyl optionally substituted by one or more of lower alkyl of from one to four carbons, halogen, trifluoromethyl, cyano, NH$_2$, NHR$^{11}$ wherein R$^{11}$ is C$_{1-4}$alkyl, NHCOR$^{11}$ wherein R$^{11}$ is as defined above, carboxy, alkoxycarbonyl wherein the alkoxy is of from one to four carbons, alkylthio wherein the alkyl is of from one to four carbons, nitro, acyl of from two to four carbons, hydroxy, C$_{1-6}$-alkoxy, CH$_2$CO$_2$R' wherein R' is hydrogen or C$_{1-6}$-alkyl which may be branched, CH$_2$CN, CH$_2$CONR$^{IV}$R$^V$ wherein R$^{IV}$ and R$^V$ independently are hydrogen or C$_{1-6}$-alkyl, optionally branched; aralkyl which is aryl as defined above attached through C$_{1-4}$alkyl; R$^5$ is NO$_2$, F, CF$_3$, SO$_2$NR''R''' wherein R'' and R''' independently are hydrogen or C$_{1-6}$-alkyl, or CN; and R$^4$, R$^6$, R$^7$ independently are hydrogen, C$_{1-6}$alkyl which may be branched, phenyl, halogen, C$_{1-6}$alkoxy, NO$_2$, CN, SO$_2$NR''R''' wherein R'' and R''' independently are hydrogen or C$_{1-6}$-alkyl, or CF$_3$, or R$^6$ or R$^7$ together form an additional 4 to 7 membered ring which may be aromatic or partial saturated and which may be substituted with halogen, N$_2$, CF$_3$, CN, SO$_2$NR''R''' wherein R'' and R''' independently are hydrogen or C$_{1-6}$-alkyl, and R$^4$ has the meaning set forth above.

10. A compound having the formula

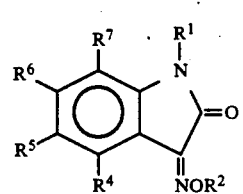

and isomers thereof wherein
R$^1$ is hydrogen,
R$^2$ is (1) alkenyl of from two to six carbon atoms, (2) alkynyl of from two to six carbons, (3) (CH$_2$)$_{1-6}$CO$_2$H, (4) (CH$_2$)$_{1-6}$CONHR wherein R is C$_{1-6}$alkyl, optionally branched; aryl which is phenyl optionally substituted by one or more of lower alkyl of from one to four carbons, halogen trifluoromethyl, cyano, carboxy, alkoxycarbonyl wherein the alkoxy is of from one to four carbons, alkylthio wherein the alkyl is of from one to four carbons, nitro, acyl of from two to four carbons, hydroxy, C$_{1-6}$-alkoxy, CH$_2$CO$_2$R' wherein R' is hydrogen or C$_{1-6}$-alkyl which may be branched, CH$_2$Cn, CH$_2$CONR$^{IV}$R$^V$ wherein R$^{IV}$ and R$^V$ independently are hydrogen or C$_{1-6}$-alkyl, optionally branched; aralkyl which is aryl as defined above attached through C$_{1-4}$alkyl; or SO$_2$R$^{10}$ wherein R$^{10}$ is C$_{1-12}$alkyl, optionally branched; aryl which is phenyl optionally substituted by one or more of lower alkyl of from one to four carbons, halogen, trifluoromethyl, cyano, NH$_2$, NHR$^{11}$ wherein R$^{11}$ is C$_{1-4}$alkyl, NHCOR$^{11}$ wherein R$^{11}$ is as defined above, carboxy, alkoxycarbonyl wherein the alkoxy is of from one to four carbons, alkylthio wherein the alkyl is of from one to four carbons, nitro, acyl of from two to four carbons, hydroxy, C$_{1-6}$-alkoxy, CH$_2$CO$_2$R' wherein R' is hydrogen or C$_{1-6}$alkyl which may be branched, CH$_2$CN, CH$_2$CONR$^{IV}$R$^V$ wherein R$^{IV}$ and R$^V$ independently are hydrogen or C$_{1-6}$-alkyl, optionally branched; aralkyl which is aryl as defined above attached through C$_{1-4}$alkyl; R$^5$ is NO$_2$, F, CF$_3$, SO$_2$NR''R''' wherein R'' and R''' independently are hydrogen or C$_{1-6}$-alkyl, or CN; and R$^4$, R$^6$, R$^7$ independently are hydrogen, C$_{1-6}$-alkoxy, NO$_2$, CN, SO$_2$NR''R''' wherein R'' and R''' independently are hydrogen or C$_{1-6}$alkyl, or CF$_3$, R$^6$ and R$^7$ together form an additional 4 to 7 membered ring which may be aromatic or partial saturated and which may be substituted with halogen, NO$_2$, CF$_3$, CN, SO$_2$NR''R''' wherein R'' and R''' independently are hydrogen or C$_{1-6}$-alkyl, and R$^4$ has the meaning set forth above; and that R$^5$ is different from NO$_2$ and F when R$^1$, R$^4$, R$^6$, and are hydrogen; and that R$^5$ is different from NO$_2$ when R$^1$, R$^4$, and R$^6$ are hydrogen and R$^7$ is not other than NO$_2$.

11. A compound according to claim 9 or 10 wherein $R^4$ and $R^5$ independently are hydrogen, F, $NO_2$, CN, $CF_3$, or $SO_2NR''R'''$ wherein $R''$ and $R'''$ independently are hydrogen or $C_{1-6}$-alkyl, and wherein $R^6$ and $R^7$ together form an additional 4 to 7 membered ring which may be aromatic or partial saturated and which may be substituted with halogen, $NO_2$, $CF_3$, CN, $SO_2NR''R'''$ wherein $R''$ and $R'''$ independently are hydrogen or $C_{1-6}$-alkyl.

12. A compound according to claim 11 wherein the additional ring formed by $R^6$ and $R^7$ is substituted with halogen, $NO_2$, $CF_3$, CN, or $SO_2NR''R'''$ wherein $R''$ and $R'''$ independently are hydrogen or $C_{1-6}$-alkyl.

13. A method of treating a central nervous system disorder in a subject in need of such treatment, comprising the step of administering to said subject an effective amount of a compound having the formula

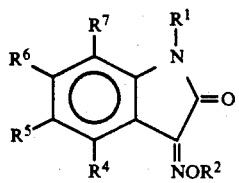

and isomers thereof wherein $R^1$ is hydrogen, $C_{1-6}$-alkyl which may be branched, $C_{3-7}$-cycloalkyl, benzyl, phenyl which may be substituted, acyl, hydroxy, $C_{1-6}$alkoxy, $CH_2CO_2R'$ wherein $R'$ is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, or $CH_2C(=NOH)NH_2$;

$R^2$ is (1) alkenyl of from two to six carbon atoms, (2) alkynyl of from two to six carbons, (3) $(CH_2)_{1-6}CO_2H$, (4) $(CH_2)_{1-6}CONHR$ wherein R is $C_{1-6}$alkyl, optionally branched; aryl which is phenyl optionally substituted by one or more of lower alkyl of from one to four carbons, halogen, trifluoromethyl, cyano, carboxy, alkoxycarbonyl wherein the alkoxy is of from one to four carbons, alkylthio wherein the alkyl is of from one to four carbons, nitro, acyl of from two to four carbons, hydroxy, $C_{1-6}$-alkoxy, $CH_2CO_2R'$ wherein $R'$ is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, optionally branched; aralkyl which is aryl as defined above attached through $C_{1-4}$alkyl; or $SO_2R^{10}$ wherein $R^{10}$ is $C_{1-12}$alkyl, optionally branched; aryl which is phenyl optionally substituted by one or more of lower alkyl of from one to four carbons, halogen, trifluoromethyl, cyano, $NH_2$, $NHR^{11}$ wherein $R^{11}$ is $C_{1-4}$alkyl, $NHCOR^{11}$ wherein $R^{11}$ is as defined above, carboxy, alkoxycarbonyl wherein the alkoxy is of from one to four carbons, alkylthio wherein the alkyl is of from one to four carbons, nitro, acyl of from two to four carbons, hydroxy, $C_{1-6}$-alkoxy, $CH_2CO_2R'$ wherein $R'$ is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, optionally branched; aralkyl which is aryl as defined above attached through $C_{1-4}$alkyl;

$R^5$ is $NO_2$, F, $CF_3$, $SO_2NR''R'''$ wherein $R''$ and $R'''$ independently are hydrogen or $C_{1-6}$-alkyl, or CN; and $R^4$, $R^6$, $R^7$, independently are hydrogen, $C_{1-6}$-alkyl which may be branched, phenyl, halogen, $C_{1-6}$-alkoxy, $NO_2$, CN, $SO_2NR''R'''$ wherein $R''$ and $R'''$ independently are hydrogen or $C_{1-6}$-alkyl, or $CF_3$, or $R^6$ and $R^7$ together form an additional 4 to 7 membered ring which may be substituted with halogen, $NO_2$, $CF_3$, CN, $SO_2NR''R'''$ wherein $R''$ and $R'''$ independently are hydrogen or $C_{1-6}$-alkyl, and $R^4$ has the meaning set forth above; and that $R^5$ is different from $NO_2$ and F when $R^1$, $R^4$, $R^6$, and are hydrogen and and that $R^5$ is different from $NO_2$ when $R^1$, $R^4$ and $R^6$ are hydrogen and $R^7$ is $NO_2$.

14. A method of antagonizing the biological effects of an excitatory amino acid of a subject in need of such antagonization comprising the step of administering to said subject an effective excitatory amino acid antagonizing amount of a compound having the formula

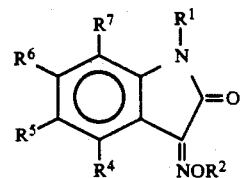

and isomers thereof wherein
$R^1$ is hydrogen, $C_{1-6}$-alkyl which may be branched, $C_{3-7}$-cycloalkyl, benzyl, phenyl which may be substituted, acyl, hydroxy, $C_{1-6}$-alkoxy, $CH_2CO_2R'$ wherein $R'$ is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, or $CH_2C(=NOH)NH_2'$ $R^2$ is (1) alkenyl of from two to six carbon atoms, (2) alkynyl of from two to six carbons, (3) $(CH_2)_{1-6}CO_2H$, (4) $(CH_2)_{1-6}CONHR$ wherein R is $C_{1-6}$alkyl, optionally branched; aryl which is phenyl optionally substituted by one or more of lower alkyl of from one to four carbons, halogen trifluoromethyl, cyano, carboxy, alkoxycarbonyl wherein the alkoxy is of from one to four carbons, alkylthio wherein the alkyl is of from one to four carbons, nitro, acyl of from two to four carbons, hydroxy, $C_{1-6}$-alkoxy, $CH_2CO_2R'$ wherein $R'$ is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, optionally branched; aralkyl which is aryl as defined above attached through $C_{1-4}$alkyl; or so $SO^2R^{10}$ wherein $R^{10}$ is $C_{1-12}$alkyl, optionally branched; aryl which is phenyl optionally substituted by one or more of lower alkyl of from one to four carbons, halogen trifluoromethyl, cyano, $NH_2$, $NHR^{11}$ wherein $R^{11}$ is $C_{1-4}$alkyl, $NHCOR^{11}$ wherein $R^{11}$ is as defined above, carboxy, alkoxycarbonyl wherein the alkoxy is of from one to four carbons, alkylthio wherein the alkyl is of from one to fur carbons,nitro acyl of from two to fur carbons, hydroxy, $C_{1-6}$-alkoxy, $CH_2CO_2R'$ wherein $R'$ is hydrogen or $C_{1-6}$alkyl which may be branched, $CH_2CN$, $CH_2CONR^{IV}R^V$ wherein $R^{IV}$ and $R^V$ independently are hydrogen or $C_{1-6}$-alkyl, optionally branched; aralkyl which is aryl as defined above attached through $C_{1-4}$alkyl;

$R^4$, $R^5$, $R^6$, $R^7$ independently are hydrogen, $C_{1-6}$-alkoxy, $NO_2$CN, $SO_2NR'R'''$ wherein $R''$ and $R'''$ independently are hydrogen or $C_{1-6}$alkyl, or $CF_3$;

or $R^6$ and $R^7$ together form an additional 4 to 7 membered ring which may be aromatic or partial saturated and which may be substituted with halogen, $NO_2$, $CF_3$, CN, $SO_2NR''R'''$ wherein $R''$ and $R'''$ independently are hydrogen or $C_{1-6}$-alkyl, and $R^4$ and $R^5$ have the meanings set forth above, for the preparation of a medicament useful in the treatment of conditions sensitive to an excitatory amino acid in unit dosage form.

15. The method according to claim 14 wherein at least one of $R^4$, $R^5$, $R^6$, or $R^7$ is an electron withdrawing substituent selected from the group consisting of $NO_2$, $CF_3$, CN, $SO_2NR''R'''$, or halogen and $R^1$, $R^2$, $R^4$, $R^5$, $R^6$, , $R''$, and $R'''$ otherwise have the meanings set forth in claim 14.

16. A pharmaceutical composition for use in antagonizing the biological effects of an excitatory amino acid of a subject in need of such antagonization comprising an effective excitatory amino acid antagonizing amount of a compound having the formula

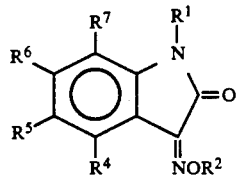

and isomers thereof wherein $R^1$ is hydrogen, $C_{1-6}$-alkyl which may be branched, $C_{3-7}$-cycloaklyl, benzyl, phenyl which may be substituted, acyl, hydrocy, $C_{1-6}$-alkoxy, $CH_2CO_2R'$ wherein $R'$ is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, or $CH_2C(=NOH)NH_2$;

$R^2$ is (1) alkenyl of from two to six carbon atoms, (2) alkynyl of from two to six carbons, (3) $(CH_2)_{1-6}CO_2H$, (4) $(CH_2)_{1-6}CONHR$ wherein R is $C_{1-6}$-alkyl, optionally branched; aryl which is phenyl optionally substituted by one or more of lower alkyl of from one to four carbons, halogen trifluoromethyl, cyano, carboxy, alkoxycarbonyl wherein the alkoxy is of from one to four carbons, alkylthio wherein the alkyl is of from one to four carbons, nitro, acyl of from two to four carbons, hydroxy, $C_{1-6}$-alkoxy, $CH_2CO_2R'$ wherein $R'$ is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, optionally branched; aralkyl which is aryl as defined above attached through $C_{1-4}$alkyl; or $SO_2R^{10}$ wherein $R^{10}$ is $C_{1-12}$alkyl, optionally branched; aryl which is phenyl optionally substituted by one or more of lower alkyl of from one to four carbons, halogen, trifluoromethyl, cyano, $NH_2$, $NHR^{11}$ wherein $R^{11}$ is $C_{1-4}$alkyl, $NHCOR^{11}$ wherein $R^{11}$ is as defined above, carboxy, alkoxycarbonyl wherein the alkoxy is of from one to four carbons, alkylthio wherein the alkyl is of from one to four carbons, nitro, acyl of from two to four carbons, hydroxy, $C_{1-6}$-alkoxy, $CH_2CO_2R'$ wherein $R'$ is hydrogen or $C_{1-6}$-alkyl which may be branched, $C_2CN$, $CH_2CONR^{IV}R^V$ wherein $R^{IV}$ and $R^V$ independently are hydrogen or $C_{1-6}$-alkyl, optionally branched; aralkyl which is aryl as defined above attached through $C_{1-4}$-alkyl;

$R^4$, $R^5$, $R^6$, $R^7$, independently are hydrogen, $C_{1-6}$-alkyl which may be branched, phenyl, halogen, $C_{1-6}$-alkoxy, $NO_2$, CN, $SONR''R'''$ wherein $R''$ and $R'''$ independently are hydrogen or $C_{1-6}$-alkyl, or $CF_3$; or $R^6$ or $R^7$ together form an additional 4- to 7-membered ring which may be aromatic or partial saturated and which may be substituted with halogen, $NO_2$, $CF_3$, CN, $SO_2NR''R'''$ wherein $R''$ and $R'''$ independently are hydrogen or $C_{1-6}$-alkyl, and $R^4$ and $R^5$ have the means set forth above together with a pharmaceutical carrier.

* * * * *